United States Patent [19]

Huber

[11] 4,404,288

[45] Sep. 13, 1983

[54] METHOD AND APPARATUS FOR CONCENTRATING A VAPOR OF A MERCURY SAMPLE SOLUTION

[75] Inventor: Bernhard Huber, Uberlingen, Fed. Rep. of Germany

[73] Assignee: The Perkin-Elmer Corporation, Norwalk, Conn.

[21] Appl. No.: 371,635

[22] Filed: Apr. 26, 1982

Related U.S. Application Data

[63] Continuation-in-part of Ser. No. 191,567, Sep. 29, 1980, abandoned.

[30] Foreign Application Priority Data

Oct. 25, 1979 [DE] Fed. Rep. of Germany ....... 2943092

[51] Int. Cl.³ .................. G01N 23/00; G01N 27/00
[52] U.S. Cl. ................................ 436/177; 204/1 T;
    204/434; 422/78; 422/80; 436/81; 436/155
[58] Field of Search ............ 436/81, 155, 177;
    204/1 T, 195 R, 105 R, 124, 434; 422/78, 80

[56] References Cited

U.S. PATENT DOCUMENTS

| 3,852,604 | 12/1974 | Grengg ........................ 250/373 |
| 3,884,639 | 5/1975 | Sugiyama ..................... 436/81 |
| 4,023,929 | 5/1977 | Becker et al. ................ 436/81 |
| 4,295,854 | 10/1981 | Huber ........................ 23/230 PC |

OTHER PUBLICATIONS

F. Mollwo Perkin, Trans. Faraday Soc., vol. 5, pp. 45-48, (1909).

Primary Examiner—G. L. Kaplan
Attorney, Agent, or Firm—S. A. Giarratana; F. L. Masselle; R. A. Hays

[57] ABSTRACT

A method for concentrating a vapor of a mercury sample solution is carried out by an apparatus having an electrode of amalgam-forming material which electrode is movable from the sample solution to a heated portion within a tube.

13 Claims, 1 Drawing Figure

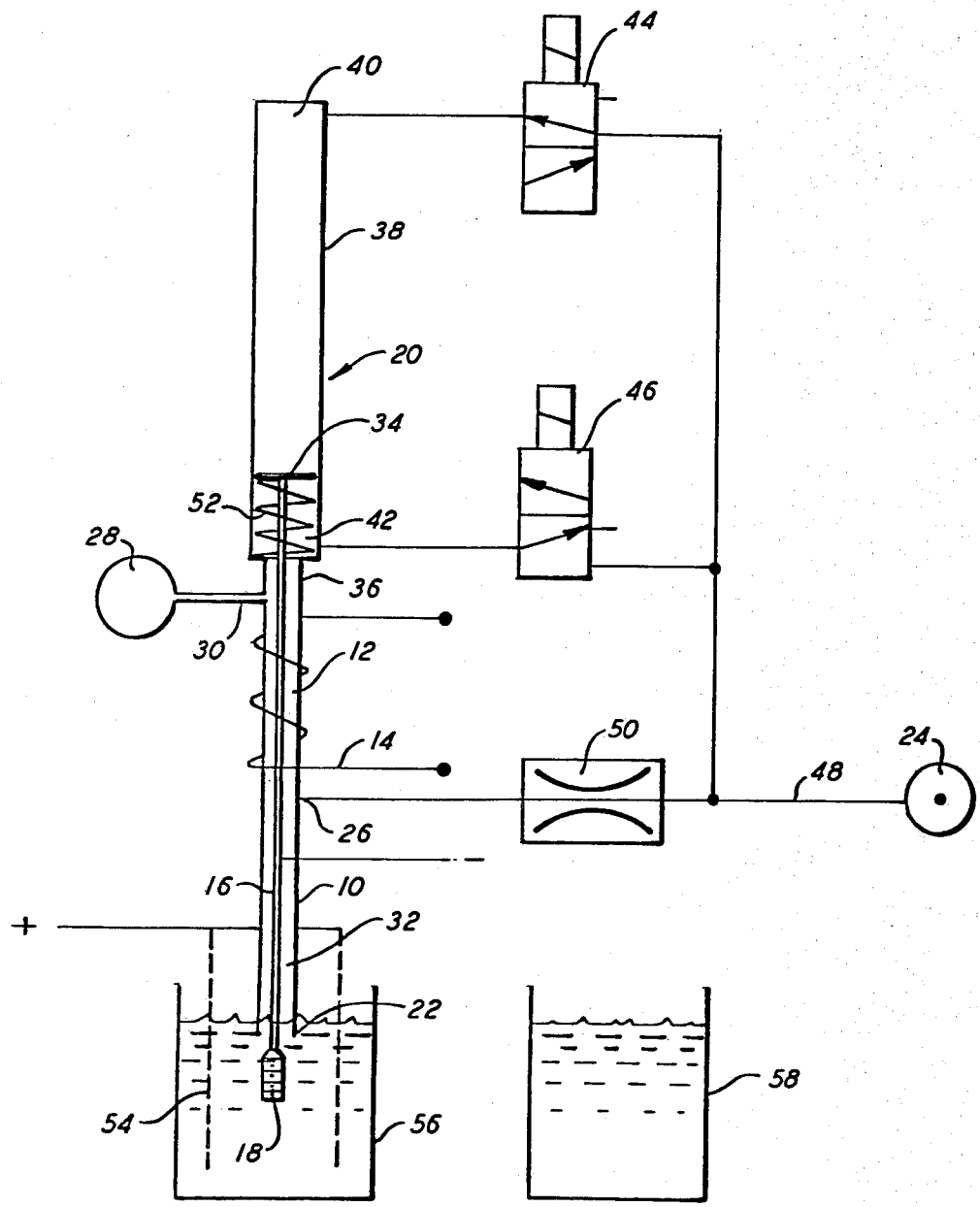

METHOD AND APPARATUS FOR CONCENTRATING A VAPOR OF A MERCURY SAMPLE SOLUTION

BACKGROUND OF THE INVENTION

This Application is a continuation-in-part of now abandoned U.S. Application Ser. No. 191,567, filed Sept. 29, 1980.

The present invention generally relates to a method for concentrating a vapor of a mercury sample solution and an apparatus for carrying out that method and, in particular, relates to such a method wherein a sample solution is electrolyzed to separate elemental mercury therefrom.

It is often desirable to measure the amount of mercury in a solution by means of atomic absorption spectroscopy. While atomic absorption spectroscopic methods are extremely accurate, it is nevertheless somewhat enigmatic to obtain sufficient mercury vapor for accurate measurement when the sample solution contains small amounts of mercury.

Conventionally, the mercury vapor produced by chemical reduction, for example, by use of $SnCl_2$ or $NaBH_4$, is passed over silver or gold wool to produce a concentrated sample. In such a method, the mercury from the vapor forms an amalgam with the silver or gold, which amalgam is subsequently heated to drive off a more concentrated vapor of mercury. This concentrated vapor is then conveyed into a measuring cell. However, such a technique has a major drawback in that the reducing agent itself can contain mercury and thus severely inhibit the accuracy of the sample measurement.

SUMMARY OF THE INVENTION

Accordingly, it is one object of this invention to produce a mercury vapor which accurately represents the amount of mercury in the sample solution. This object is achieved by separating elemental mercury from a sample solution by electrolyzing the solution using an electrode of an amalgam-forming material. The electrode is movable to a position whereat it can be heated to drive off a concentrated mercury vapor.

It is another object of the invention to provide an apparatus designed to carry out the above-stated method.

These and other objects will become apparent from the following drawing and specification.

BRIEF DESCRIPTION OF THE DRAWING

The single FIGURE of the drawing is a diagrammatic representation of an apparatus, not drawn to scale, embodying the principles of the present invention and capable of carrying out the method according to the invention.

DETAILED DESCRIPTION OF THE INVENTION

An apparatus, embodying the principles of the present invention, comprises a tube 10 having a region 12 which is adapted to be heated by a heater 14. The apparatus includes a rod 16 having, at one end thereof, an electrode 18 formed of amalgam-forming material. Preferably, the electrode 18 is formed from platinum, although gold or silver may also be used. The rod 16 is adapted to move lengthwise within the tube 10 by a positioning mechanism 20. In this embodiment, the rod 16 is moved between a first position and a second position. Specifically in the first position, that which is illustrated in the drawing, the electrode projects from one end 22 of the tube 10. The second position of the rod 16 locates the electrode 18 thereof in the region 12 of the tube 10.

A gas inlet 26, which is connected to a source 24 of carrier gas, which may be inert, opens into the tube 10 between the one end 22 and the region 12. A gas outlet conduit 30 extends from the tube 10 to an element measuring means 28, which means can be an atomic absorption spectrometer. As indicated, the gas outlet 30 extends from the tube 10 beyond the region 12 of the heater 14 when viewed from the gas inlet 26.

Preferably the region 12, heated by the heater 14, is distal from the one end 22 and is spaced apart therefrom by an unheated region 32 of the rod 16. The positioning mechanism 20 can include a rod position intermediate the first and the second positions whereat the electrode 18 lies in the unheated region 32 of the tube 10. The positioning mechanism 20 can include a dual-acting positioning piston 34 positioned and guided by a piston cylinder 38 located at the other end 36 of the tube 10. The piston 34 is preferably coaxial with the tube 10 and is cooperatively connected to the rod 16 therein. Piston cylinder chambers 40 and 42 are formed on opposite sides of the positioning piston 34. The cylinder chambers 40 and 42 are each connected, via solenoid valves 44 and 46 respectively, to an inlet conduit 48 for a pressurized gas, which for convenience can be connected to the source 24 of the carrier gas. In this embodiment the carrier gas also serves as the pressurized gas for controlling the position of the piston 34. The inlet conduit 48 is connected to the gas inlet 26 of the tube 10 via a throttle mechanism 50. The positioning piston 34 is secured in its intermediate position by a spring 52. When either chamber 40 or 42 is acted upon by pressure from the carrier gas source the piston 34 moves the rod 16 a distance along the tube 10 in accordance with that pressure.

The tube 10 and the rod 16 therein are electrically insulated from each other. In addition, an anode 54 is fitted to the one end 22 of the tube 10. The anode 54 is connected to the positive terminal of a source of electric current (not shown) and the rod 16 is connected to the negative terminal thereof. Preferably, the anode 54 is formed of platinum, or the like. In addition, it is preferably formed as a cylindrically shaped grid and positioned so as to coaxially surround the one end 22 of the tube 10. When the rod 16 is in the first position, the electrode 18 projects from the one end 22 and acts as a cathode with respect to the anode 54. The method for utilizing the above-described apparatus is described below.

An acidified test solution, for example, which is to be tested for the presence of mercury is poured into a test vessel 56. The anode 54 and the one end of the tube 22 are then dipped into the test solution. The solenoid valve 44 is opened and the electrode 18, via operation of the piston 34, is located in the first position and thus extends into the test solution. While the electrode 18 is located in the test solution, a current is generated and flows from the anode 54 to the cathode (i.e., electrode 18) via the test solution. As a result of this current flow an amalgam is formed on the electrode 18. After a predetermined number of ampere-seconds the solenoid 44 is closed and the positioning piston 34, under the influence of the spring 52, is positioned at the intermediate position. The electrode 18 is thereby drawn from the test solution and held in the unheated, or intermediate, portion 32 of the tube 10. In this position, the apparatus may now be immersed in a second vessel 58 filled with, for example, distilled water and the electrode 18 extended once again by opening the solenoid valve 44. The electrode 18 can thus be rinsed to remove excess test solution therefrom.

After rinsing the electrode 18, the solenoid valve 44 is switched off and the solenoid valve 46 is energized. The positioning piston 34 is thus moved to position the electrode 18 within the heated region 12 of the tube 10. The heater is energized, and the electrode 18 is thereby heated. The elemental mercury of the amalgam is driven off during the heating process. The mercury vapor thus formed, is conveyed by the flow of carrier gas from the source 24, via the throttle 50 through the gas inlet 26, into the measuring means 28. Of course, the electrode 18 can be moved from the extended position directly to the heated region 12 of the tube 10 without being rinsed if it is so desired.

In the case of very small amounts of mercury in the test solution a small amount of amalgam-forming material may be added to facilitate the formation of the amalgam on the electrode 18. While the addition of a small amount of amalgam-forming material to the solution can be accomplished by any known means in the art, it is preferred that about 0.1 grams/liter of gold chloride be added to the solution. Alternatively, a coating layer of gold, approximately two micrometers thick, can be formed by known means on the platinum electrode 18.

The apparatus described herein can be an accessory to, and used in cooperation with, an atomic absorption spectrometer. Advantageously, since no reducing agents are required, there is no blank value to contend with or to cause erroneous results.

Alternatively, the apparatus can be equipped with an optical system and thus be used solely as an independent apparatus for the determination of the mercury concentration of a test solution. The apparatus described herein is readily adaptable to automation, in particular, the dipping of the electrode 18 into a test solution vessel or rinsing vessel is a straightforward motion which can be easily automated by mechanisms well known in the present art.

While the particular apparatus and method detailed herein relate specifically to the measurement of a small sample of mercury, many variations can be designed which encompass the principles of the present invention. Therefore, the embodiment described herein is considered exemplary only and is not to be construed as limiting the scope of the invention. The scope of the present invention is limited only as it is defined in the appended claims.

What is claimed is:

1. A method of concentrating small amounts of mercury from a solution, said method comprising the steps of:
    introducing a concentration of amalgam-forming material to said solution;
    electrolyzing, by employing an electrode of amalgam-forming material, said solution to separate elemental mercury from said solution and form an amalgam thereof on said electrode;
    heating said amalgam to form a concentrated mercury vapor; and
    capturing said mercury vapor in a means for measuring said mercury.

2. A method as claimed in claim 1 further comprising the step of:
    rinsing said amalgam after said forming electrolyzing step and before said heating step.

3. An apparatus for concentrating small amounts of mercury from a test solution, said apparatus comprising:
    a hollow tube having means associated therewith for heating a portion thereof;
    a rod, slidably mounted within said tube, having an electrode of amalgam-forming material at one end thereof; and
    means for positioning said rod within said tube between a first position whereat said electrode can be inserted in said test solution whereby an amalgam can be formed on said electrode and a second position whereat said electrode is located in said portion of said tube having means for heating associated therewith, whereby, when said portion is heated, a concentrated mercury vapor is driven off from said amalgam.

4. An apparatus as claimed in claim 3 wherein said positioning means is adapted to position said electrode at a third position intermediate said first and said second positions whereat said electrode is located in an unheated portion of said tube.

5. An apparatus as claimed in claim 4 further comprising a rinse solution.

6. An apparatus as claimed in claim 4 further comprising:
    a first vessel for retaining said test solution; and a second vessel for retaining said test solution; and a second vessel for retaining said rinse solution.

7. An apparatus as claimed in claim 3 wherein said means for positioning said rod includes a dual-acting positioning piston located in and guided by a piston cylinder at the other end of said tube, said piston being coaxial with said rod in said tube, said piston forming, on opposite sides thereof, two cylinder chambers with said piston cylinder, said chambers being connected, each via a solenoid valve, to a source of pressurized gas, said positioning piston being responsive to gaseous pressure in either chamber.

8. An apparatus as claimed in claim 3 further comprising means for introducing a carrier gas into said tube; and
    means for providing an outlet from said tube for said carrier gas whereby when said mercury vapor is formed it can be transported away from said tube via said carrier gas.

9. An apparatus as claimed in claim 8 wherein:
    said introduction means includes a source of carrier gas and an inlet gas conduit between said source and said tube, said inlet gas conduit contacts said tube between said heated portion and said one end thereof; and
    said outlet providing means being positioned along said tube such that said carrier gas, when introduced, flows through at least a segment of said heated portion.

10. An apparatus as claimed in claim 9 wherein said inlet gas conduit is connected between said source of protective gas and said tube via a throttle.

11. An apparatus as claimed in claim 3 wherein said tube and said rod are electrically isolated from each other; and
    an anode is affixed to said one end of said tube.

12. An apparatus as claimed in claim 11 wherein said anode is platinum.

13. An apparatus as claimed in claim 11 wherein said anode is a cylindrical grid coaxially surrounding said one end of said tube.

* * * * *